United States Patent
Otaki et al.

(10) Patent No.: US 6,644,094 B1
(45) Date of Patent: Nov. 11, 2003

(54) TRACTION COEFFICIENT MEASUREMENT DEVICE

(75) Inventors: Ryoichi Otaki, Fujisawa (JP); Hiroya Achiha, Hiratsuka (JP); Shinichi Natsumeda, Yokohama (JP)

(73) Assignee: NSK Ltd., Tokyo (JP)

( * ) Notice: Subject to any disclaimer, the term of this patent is extended or adjusted under 35 U.S.C. 154(b) by 0 days.

(21) Appl. No.: 09/547,994

(22) Filed: Apr. 12, 2000

(30) Foreign Application Priority Data

Apr. 13, 1999 (JP) .......................................... 11-104956
Apr. 13, 1999 (JP) .......................................... 11-105567

(51) Int. Cl.[7] ........................ G01N 19/02; G01M 13/02
(52) U.S. Cl. ................................................ 73/9; 73/10
(58) Field of Search ........................................ 73/9, 10

(56) References Cited

U.S. PATENT DOCUMENTS

| | | | | |
|---|---|---|---|---|
| 3,209,589 A | * | 10/1965 | Schletter ........................ | 73/9 X |
| 3,823,599 A | * | 7/1974 | Litz et al. ........................ | 73/10 |
| 3,918,468 A | * | 11/1975 | Stenge ........................... | 73/9 X |
| 3,946,593 A | * | 3/1976 | Ruget ............................. | 73/10 |
| 5,076,567 A | * | 12/1991 | Sasaki et al. .................. | 271/265 |

FOREIGN PATENT DOCUMENTS

GB 2194060 A * 2/1988 ................. 73/53.05

OTHER PUBLICATIONS

Derwent–Acc–No; 1983–806779 (SU 987477 A) Inventor Krovchenko et al. "Finding Maize Cub Capture Angle Between Rollers—by Using Driver Text Rollers for Yielding Gap and Frictional Information", Jan. 1983.*

Muraki et al., "Influence of Geometry and Materials of the Rollers on EHD Traction", *Journal of Japanese Society of Tribologists*, vol. 37, No. 10, pp. 839–845 Oct. 1992.

Poon et al., "Frictional Behavior of Lubricated Rolling–Contact Elements", Proc. Instn. Mech. Engrs, vol. 181 Pt. 1 No. 16, pp. 363–389 (1967) Month not given.

Tevaarwerk, "A Simple Thermal Correction for Large Spin Traction Curves", Transactions of the ASME, vol. 103, pp. 440–446, Apr. 1981.

Terauchi et al., "Behavior of Lubricants in Elastohydrodynamic Lubrication", *Lubrication*, vol. 32, No. 11, pp. 811–817 Jan. 1987.

Saitoh et al., "Effects of the Geometry and Size of the Rollers and Skew Component on EHL Traction", Technical Report C of the Japanese Society of Mechanical Engineers, vol. 57, No. 533, pp. 277–282 (1991) Month not given.

* cited by examiner

*Primary Examiner*—Thomas P. Noland
(74) *Attorney, Agent, or Firm*—Crowell & Moring LLP

(57) ABSTRACT

The present invention provides a traction coefficient measurement device having a driving roller rotated around a driving shaft, a driven shaft is rotated together with a driven shaft, corresponding to the rotation of the driving roller, based on the engagement with the driving roller, and a load device for applying a resistance to the driven shaft against the rotation, wherein the driving shaft is fixed in position and the driven shaft is supported so as to move to and from the driving shaft, and a press apparatus is used to force the driven shaft to the driving shaft for measurement operation, and the driven shaft is positioned lower than the driving shaft in height, and the traction force acting on the engagement portion between the driving roller and the driven roller is directed in a direction to push the driven shaft downward.

12 Claims, 13 Drawing Sheets

TRACTION COEFFICIENT MEASUREMENT DEVICE

FIELD OF THE INVENTION

The present invention relates to a traction coefficient measurement device.

BACKGROUND OF THE INVENTION

A power transmission means used in various machines and apparatus comprises a friction transmission or traction drive transmission, and a traction coefficient measurement device is utilized to measure a traction coefficient which affects the essential performance of the friction transmission or traction drive transmission.

For example, as a transmission for automobiles, helicopters, or ships, the utilization of an endless transmission of the toroidal type, that is a kind of traction drive transmission, is developed. In addition, the traction drive transmission is used for a spindle of the machine tools.

The traction drive transmission has a traction section that is an engagement portion where power transmitting members are provided in friction-engagement with each other, and the measurement of the traction coefficient of the traction section is important for design of the high performance traction drive transmission.

Conventionally used for this purpose is a traction coefficient measurement device which has a pair of rollers, that is driving roller and driven roller installed therein, the peripheral surfaces of which are engaged with each other for transmitting a rotational force.

There are two methods for measuring the traction coefficient using a pair of rollers.

In the first method, a driving roller drives a driven roller to rotate with, a load applied thereto, and slippage rate in the traction section is obtained from the rotation number of the driving and driven rollers, while the traction force is obtained in the traction section from the torque applied to the driving roller.

In the second method, a pair of rollers are driven to rotate with a different rotation number or peripheral speed, and a predetermined slippage rate is forcibly added to the traction section, and the traction force at the traction section is obtained from the torque applied to the driving roller.

In the methods mentioned above for measuring the traction force, one of the drive shaft and driven shaft, the drive shaft rotating with the driving roller and the driven shaft rotating with the driven roller, is fixed in position while the other shaft is supported so as to move to and from the one shaft. While the other shaft is forced against the one shaft through a press device, the traction force is measured.

For this measurement, the traction coefficient measurement device has a surface plate, and a support plate which is provided to rotatably support the other shaft on its upper surface, such that the support plate is movable in parallel on the surface plate in a horizontal direction by way of a translation bearing such as a linear guide or cross guide, or by way of a journal bearing with an oil film used therebetween.

In the case of the conventional traction coefficient measurement device, the driving shaft and the driven shaft are positioned at the same level in height. Accordingly, the tangent line with respect to the outer peripheral surfaces of the driving roller and driven roller extends vertically, and as the outer peripheral surfaces thereof are forced against each other, the force in the traction section is exerted in a horizontal direction.

The support plate,is provided on the upper surface of the surface plate such that it is movable in the horizontal direction by way of the translation bearing, as mentioned above, and may vibrate when any outside force is applied to it because a clearance is present within the translation bearing or an oil film is present in the journal bearing.

Specifically, in the conventional structure, the force of the press apparatus added to the other shaft as mentioned above is not intended to be utilized for stabilizing the support plate. Accordingly, the support plate may not be stable, and may vibrate during the measurement operation. Once it vibrates, the measurement results of the traction force and the traction coefficient calculated on the basis of the traction force may not be precise.

SUMMARY OF THE INVENTION

One objective of the present invention is to provide a traction coefficient measurement device by which it is possible to obtain a precise traction coefficient preventing vibration from occurring in the support plate as mentioned above.

Another objective of the present invention is to provide a traction coefficient measurement device wherein the traction coefficient can be precisely measured under a condition near the practical condition of the endless transmission of the toroidal type for automobiles.

DETAILED DESCRIPTION OF THE PREFERRED EMBODIMENTS

Figure 1:
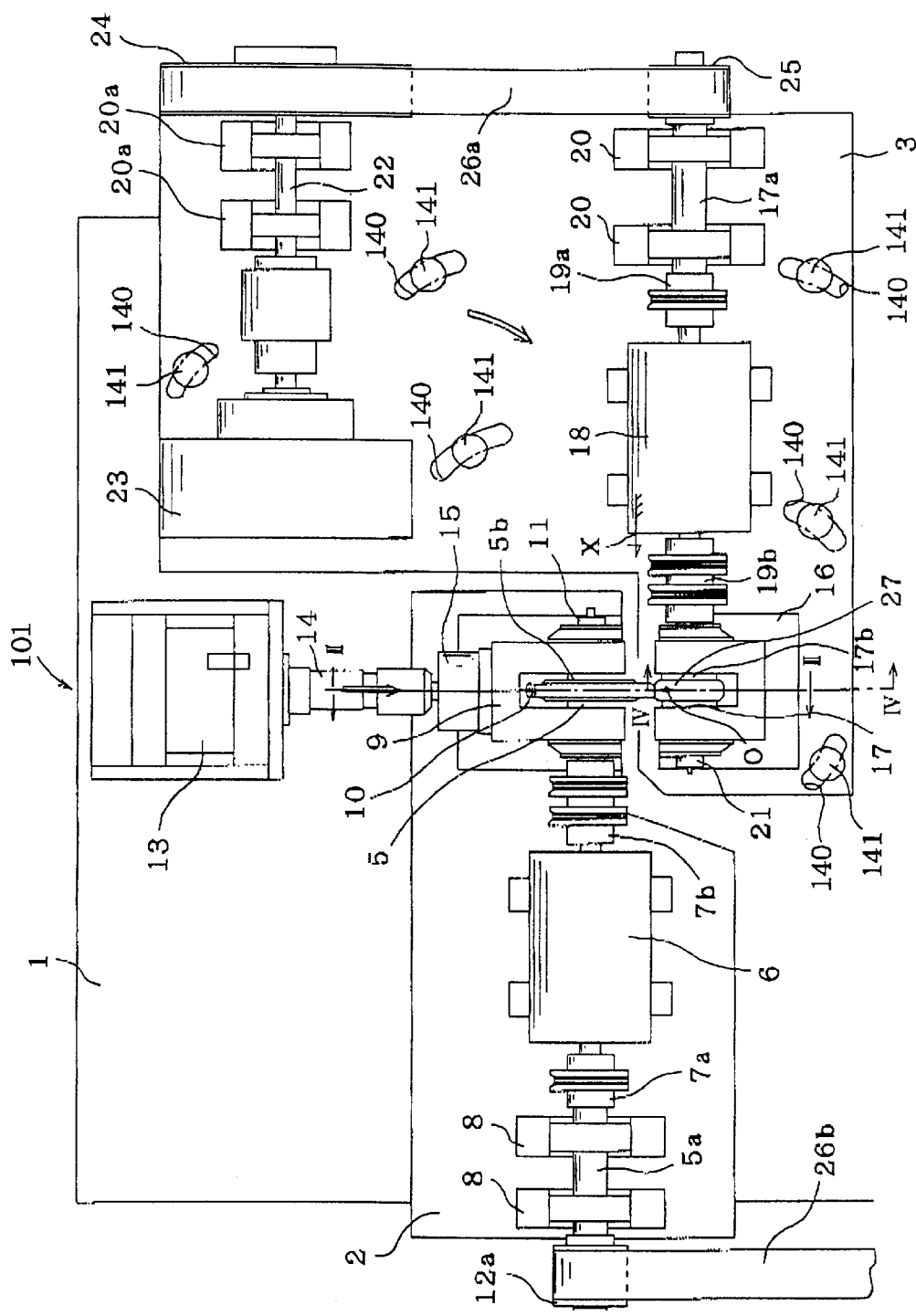
FIG. 1 is a plan view of an example of the embodiment of the traction coefficient measurement device according to the present invention.

Like the conventional traction. coefficient measurement device, the present invention provides a traction coefficient measurement device which comprises a driving roller which has an outer peripheral surface and is driven by a driving power source to rotate around a drive shaft extending in a horizontal direction, a driven roller which has an outer peripheral surface and is rotated together with a driven shaft extending in a horizontal direction, corresponding to the rotation of the driving roller, based on the engagement of its outer peripheral surface with the outer peripheral surface of the driving roller, and a load apparatus for applying a resistance to the driven shaft against the rotation of the driven shaft.

One of the driving shaft and the driven shaft is fixed in position and the other shaft is supported so as to move to and from the one shaft. And, a press apparatus is used to force the other shaft to the one shaft for measurement operation.

Particularly, with the traction coefficient measurement device, the other shaft is positioned lower than the one shaft in height.

In addition, the rotational direction of the driving roller can be controlled, so that the traction force acting on the engagement portion between the outer peripheral surface of the driving roller and the outer peripheral surface of the driven roller is directed in a direction to push the other shaft downward.

When measuring the traction coefficient with the traction coefficient measurement device of the present invention, the driving roller together with the drive shaft is driven to rotate, and the rotation of the driving roller is transmitted to the driven roller, so that the driven roller is rotated with the driven shaft.

In the structure where the other shaft is positioned lower than the one shaft in height level, the press apparatus is used to push one of the driving shaft and the driven shaft to the other shaft so as to secure surface pressure in the traction section that is the engagement portion between the outer peripheral surfaces of the both rollers. Consequently, a portion of the outer peripheral surface of the roller rotating around the other shaft, a little above the vertical center, comes into contact with a portion of the outer peripheral surface of the roller rotating around the one shaft, a little below the vertical center.

Accordingly, the tangent line with reference to the outer peripheral surface of the driving and driven rollers in the traction section is a little tilted with respect to the vertical line, the force acting on the traction section is directed in a direction a little tilted with respect to the horizontal direction.

Particularly, the force acting on the outer peripheral surface of the roller rotating with the other shaft is directed a little downward with respect to the horizontal direction. As a result, the portion for supporting the other shaft is pushed downward, so that this portion hardly vibrates.

In the structure where the rotational direction of the driving roller is controlled as mentioned above, so that the traction force acting on the engagement portion between the outer peripheral surface of the driving roller and the outer peripheral surface of the driven roller is directed in a direction to force the other shaft downward, the portion for supporting the other shaft is pushed downward, so that this portion hardly vibrates.

Now, the embodiments of the present invention are more detailed referring the attached drawings.

Figure 2:
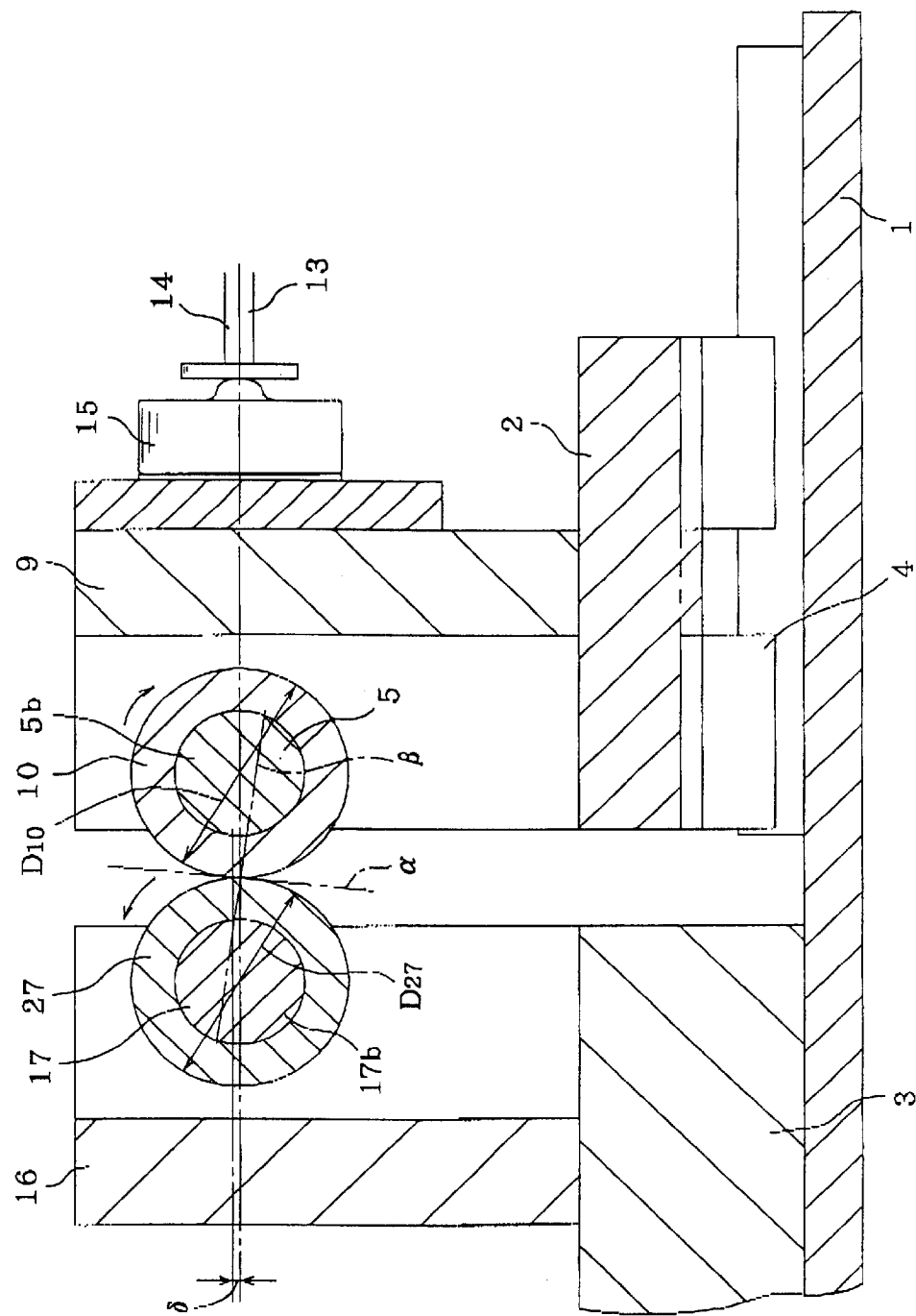
FIG. 2 is a cross sectional view taken along the line II—II of FIG. 1.

The traction coefficient measurement device according to an example of the embodiment as shown in FIGS. 1 and 2 comprises a surface plate 1 which is the upper portion of a frame 119, a support plate 2 for a unit on the driving side provided on the surface plate 1, and a support plate 3 for a unit on the driven side provided on the surface plate 1.

The support plate 2 for the unit on the driving side is movable on the surface plate 1 by way of a translation bearing 4 in a direction (upper and lower directions in FIG. 1, and left and right directions in FIG. 2) orthogonal to the arrangement direction (left and right directions in FIG. 1) of a drive shaft 5 described later. On the other hand, the support plate 3 for the unit on the driven side is fixed on the upper surface of the surface plate 1.

Rotatably supported on the upper surface of the support plate 2 for the unit on the driving side is a drive shaft 5 which has a base end portion 5a and a tip end portion 5b arranged concentric to each other.

A torque measurement device 6 on the driving side is provided between the base end portion 5a and the tip end portion 5b, and they are connected to each other in series through coupling members 7a, 7b. The base end portion 5a is rotatably supported on the support plate 2 for the unit on the driving side through a pair of rolling bearing units 8, while the tip end portion 5b is rotatably supported through a rolling bearing on a support bracket 9 wherein a driving roller 10 is fixedly supported around the middle portion of the tip end portion 5b. The support bracket 9 for the driving roller is fixed on the upper surface of the support plate 2 for the unit on the driving side and formed in a channel shape in the top plan view.

This rolling bearing has a low rolling resistance, and can bear not only a radial load but also a thrust load caused by spin, and therefore comprises at least a pair of angular ball bearings in a back to back combination or face to face combination.

Provided on the outside surface of the support bracket 9 for the driving roller is a rotation detector 11 such as rotary encoder by which the rotational speed (rotation amount) of the tip end portion 5b can be detected.

On the other hand, a driven pulley 12a is fixed to an end of the base end portion 5a, and an endless belt 26b extends between the driven pulley 12a and a driving pulley 12b which is fixed to the rotatable shaft of a motor 143 which is a driving power source.

The driving roller 10 and the drive shaft 5 have a common center shaft, and the generatrices with respect to the outer peripheral surface of the driving roller 10 extend linearly and in parallel to the rotation center of the driving roller 10. Accordingly, the outer peripheral surface of the driving roller 10 is formed in a cylindrical shape the center of which is placed in the central axis of the drive shaft 5. The driving roller 10 is supported on the support plate 2 for the unit on the driving side which is in turn supported on the surface plate 1 so as to be movable through the translation bearing 4 in a horizontal direction and in a direction orthogonal to the arrangement direction of the drive shaft 5.

A driven roller 27 is provided on the upper surface of the support plate 3 for the unit on the driven side, which is detailed later.

Provided between the upper surface of the surface plate 1 and the support bracket 9 for the driving roller is a press apparatus 13 such as air cylinder which can push the support bracket 9 toward the driven roller 27.

Specifically, the press apparatus 13 such as an air cylinder has a piston rod 14 which can be pushed in and out by way of supplying and discharging compressed air. When the piston rod 14 is projected, the support bracket 9 for the driving roller is pushed through a load measurement device 15 such as load cell to increase the contact pressure between the outer peripheral surface of the driving roller 10 and the outer peripheral surface of the driven roller 27.

Fixed at one corner (left lower portion in FIG. 1) of the support plate 3 for the unit on the driven side and at a portion facing the support bracket 9 for the driving roller is a support bracket 16 for the driven roller, by which the driven roller 27 is rotatably supported.

Rotatably supported on the upper surface of the support plate 3 for the unit on the driven side is a driven shaft 17 which comprises a base end portion 17a and a tip end portion 17b arranged concentric to each other, and a torque measurement device 18 on the driven side is provided between the base end portion 17a and the tip end portion 17b, and they are connected in series to each other through coupling members 19a, 19b.

The base end portion 17a is rotatably supported on the support plate 3 for the unit on the driven side by a pair of rolling bearing units 20, while the tip end portion 17b is rotatably supported through a rolling bearing on the support bracket 16 for the driven roller which is fixedly supported on the upper surface of the support plate 3 for the unit on the driven side and formed in a channel shape in the top plan view.

This rolling bearing used here comprises at least a pair of angular ball bearings arranged in a back to back combination or in a face to face combination.

The driven roller 27 is fixed onto the tip end portion 17b within the support bracket 16 for the driven roller.

Provided on the outside surface of the support bracket 16 for the driven roller is a rotation detector 21 on the driven side such as rotary encoder by which the rotational speed (rotation amount) of the tip end portion 17b is detected.

Rotatably supported at another corner (upper right portion in FIG. 1) of the support plate 3 for the unit on the driven side by way of rolling bearing units 20a is a load shaft 22 which produces a resistance against the rotation of the driven roller 27. The load shaft 22 has a base end portion which is connected to a load apparatus 23 such as an electromagnetic brake which provides for a resistance against the rotation of the load shaft 22.

The load apparatus 23 is cooled by a cooling means (not shown) during the operation of the traction coefficient measurement device.

The load shaft 22 has a tip end portion to which a pulley 24 is fixed, and a pulley 25 is fixed to an end of the base end portion 17a of the driven shaft 17, such that an endless belt 26a extends between the pulley 24 and the pulley 25 so as to apply the resistance of the load apparatus 23 to the driven roller 27.

In this example, the generatrices with respect to the outer peripheral surface of the driven roller 27 are formed in an arc, respectively, based on the convex surface which is defined by the outer peripheral surface of the driven roller 27.

It is desirable that the support plate 3 for the unit on the driven side which supports the driven roller 27 can be controlled in mount angle around the central axis O with reference to the surface plate 1. The central axis O vertically extends through the curvature center of one of the generatrices of the outer peripheral surface of the driven roller 27.

It should be noted that the support plate 3 for the unit on the driven side is fixed with reference to the surface plate 1 during the measurement of the traction coefficient. On the other hand, the support plate 2 for the unit on the driving side can be moved in parallel with reference to the surface plate 1 in a direction (up and down directions in FIG. 1 and left and right directions in FIG. 2) orthogonal to the arrangement direction of the drive shaft 5.

Accordingly, during the measurement, the driving roller 10 is pushed against the driven roller 27 fixed in position under a predetermined pressure by way of the press apparatus 13.

There is an oil supply nozzle 142 provided above the driving roller 10 and the driven roller 27, so that the test oil such as traction oil with its temperature controlled can be supplied to the engagement portion between the driving roller 10 and the driven roller 27.

With the traction coefficient measurement device of the present invention, the drive shaft 5 to which the driving roller 10 is fixed is placed lower in vertical position than the driven shaft 17 to which the driven roller 27 is fixed by the amount $\delta$ as shown in FIG. 2. The difference $\delta$ in vertical position between the drive shaft 5 and the driven shaft 27 is in the range from 1/20,000 to 1/2,000 of the smaller one of the diameter $D_{10}$ of the driving roller 10 and the diameter $D_{27}$ of the driven roller 27. That is, $\{1/20,000 \cdot \min(D_{10}, D_{27}) \leq \delta \leq 1/2,000 \cdot \min(D_{10}, D_{27})\}$.

In the illustrated example, the diameter $D_{10}$ of the driving roller 10 is the same to the diameter $D_{27}$ of the driven roller 27, that is $D_{10}=D_{27}$, the difference $\delta$ in vertical position is up to 1/2,000 of the diameter $D_{10}$, $D_{27}$ of the driving roller 10 and the driven roller 27. That is, $\delta \square (1/2,000)D_{10}=(1/2,000)D_{27}$.

The control of the vertical position is carried out by adjusting the vertical position of the driving shaft 5 and/or the driven shaft 17 with a shim plate while measuring the vertical position of the driving shaft 5 and the driven shaft 17.

With the present example, the rotation direction of the motor (not shown) is regulated so as to rotate the drive shaft 5 and the driving roller 10 in the counterclockwise direction in FIG. 2.

When the traction coefficient is measured with the traction coefficient measurement device of the present invention, first the mount position of the support plate 3 for the unit on the driven side is adjusted, if it is possible, with reference to the surface plate 1 to produce a predetermined spin at the engagement portion of the peripheral surfaces of the rollers 10, 27.

The degree of the spin is smaller as the drive shaft 5 and the driven shaft 17 supported on the upper surface of the support plate 3 are closer to a parallel relation to each other, and larger as the angle between the both shafts 17, 5 is larger. Once the mount position of the support plate 3 for the unit on the driven side is adjusted, the test oil at a predetermined temperature is supplied to the engagement portion between the outer peripheral surfaces of the rollers 10, 27 from the oil supply nozzle 142.

Then, the support bracket 9 for the driving roller is pressed against the driven roller 27 by way of the press apparatus 13. As a result, a predetermined contact surface pressure is exerted on the engagement portion between the outer peripheral surface of the driven roller 27 and the outer peripheral surface of the driving roller 10.

In this state, the driving roller 10 is rotated by the motor 143 through the driving pulley 12b, endless belt 26b, driven pulley 12a and drive shaft 5. During the measurement operation, a predetermined rotation speed is kept after it is reached by acceleration. Thus, when the driven roller 10 is rotated, the torque applied to the driving roller 10 is measure by the torque measurement device 6 on the driving side provided between the base end 5a and the tip end 5b of the drive shaft 5.

After the preparation as mentioned above, with the load apparatus 23 which has been produced no load, starts to gradually apply load to the driven roller 27 which is rotating. And, the measurement values obtained from the load measurement device 15, the torque measurement device 6 on the driving side, the rotation detector 11 on the driving side are processed in the operation processor, not shown, and then a curve indicating the relation between the sliding rate and the traction coefficient is obtained by a plotter, not shown. The measurement work to obtain such a curve can be carried out in real time continuously to a state of so-called gross grip where the load from the load apparatus 23 becomes large, and the driven roller 27 is not rotated while the driving roller 10 is rotated.

In this example, when the drive shaft 5 is pressed toward the driven shaft 17 with the press apparatus 13 in order to secure the surface pressure in the traction section, that is the engagement portion between the outer peripheral surface of the driving roller 10 and the outer peripheral surface of the driven roller 27, the support plate 2 for the unit on the driving side is pushed downward. Specifically, based on the differences between the vertical position of the drive shaft 5 and the vertical position of the driven shaft 17, an upper portion of the outer peripheral surface of the driving roller 10 a little higher than the vertical center thereof is engaged with a lower portion of the outer peripheral surface of the driven roller 27 a little lower than the vertical center thereof.

Accordingly, the tangent line with respect to the outer peripheral surfaces of the driving roller 10 and the driven roller 27 in the traction section, is a little tilted with respect to the vertical direction as shown with the dotted chain line α in FIG. 2. And, based on the action and reaction caused by the press apparatus 13, the direction of the force to which the traction section is subjected is a little tilted with respect to the horizontal direction as shown with the dotted chain line β. Particularly, the force applied to the outer peripheral surface of the driving roller 10 is directed a little downward with respect to the horizontal direction.

Consequently, the support plate 2 for the unit on the driving side, by which the driving roller 10 is supported through the support bracket 9 for the driving roller, is pushed downward. As a result, the support plate 2 for the unit on the driving side, which is supported by the translation bearing 4 so as to be movable on the upper surface of the surface plate 1, is hardly vibrated.

In addition, in this example, the drive shaft 5 and the driving roller 10 are rotated in the clockwise direction in FIG. 2, the traction force produced in the traction section is applied to the support plate 2 for the unit on the driving side to push it downward. Consequently, the support plate 2 for the unit on the driving side is more effectively prevented from being vibrated.

Although, the illustrated example is directed to the structure wherein, during the measurement of the traction coefficient, the support plate 3 for the unit on the driven side is fixed to the surface plate 1 while the support plate 2 for the unit on the driving side is supported so as to be movable in parallel with respect to the surface plate 1, the fixed support plate and the movable support plate can be set on the contrary.

Specifically, in FIG. 2, it can be set that the right roller is provided as the driven roller while the left roller is provided as the driving roller. In this case, the rotation center of the driven roller is set lower than the rotation center of the driving roller. And, the left roller, that is driving roller is rotated in the clockwise direction so as to rotate the right roller, that is driving roller in the counterclockwise direction, which is opposite to the previous example.

In addition, although the both conditions of the other shaft being lower than the one shaft in height and of the driven roller being regulated in the traction coefficient measurement device as mentioned above are adopted in the illustrated example, only one of the conditions can be adopted depending on the test conditions.

Incidentally, long holes 140 and bolts 141 appearing in FIG. 1 and explained later are not necessary for the examples as mentioned above.

With the traction measurement device as mentioned above, any harmful vibration can be prevented from occurring during the measurement operation, and therefore the traction coefficient can be precisely measured, which leads to improvement in performance of the friction transmission apparatus.

The following examples are related to measurement of the traction coefficient of the endless transmission of the toroidal type under the condition of the peripheral speed of the traction section: 0 to 40 m/s, the contact surface pressure Pmax: 0 to 40 Gpa, and the temperature of the traction oil: −40 to +150° C., wherein the spin caused under the practical use condition is taken into consideration.

With the traction coefficient measurement device of the following examples comprising driving and driven rollers and load apparatus as in the previous examples, at least one of the driving roller and the driven roller has an outer peripheral surface the generatrices of which form an arcuate line, respectively, to define the outer peripheral surface in a convex surface, and the portion for supporting this roller can be movable around the vertical line extending through the center of curvature of one of the generatrices.

When the traction coefficient is measured with the traction coefficient measurement device, the driving roller is driven to rotate so as to transmit the rotation of the driving roller to the driven roller.

The angle between the drive shaft and the driven shaft can be adjusted by relative displacement between the support portions of the both rollers, and the spin of the traction section can be adjusted by controlling the angle. Accordingly, the traction coefficient can be precisely measured under conditions near the practical conditions.

Figure 7:
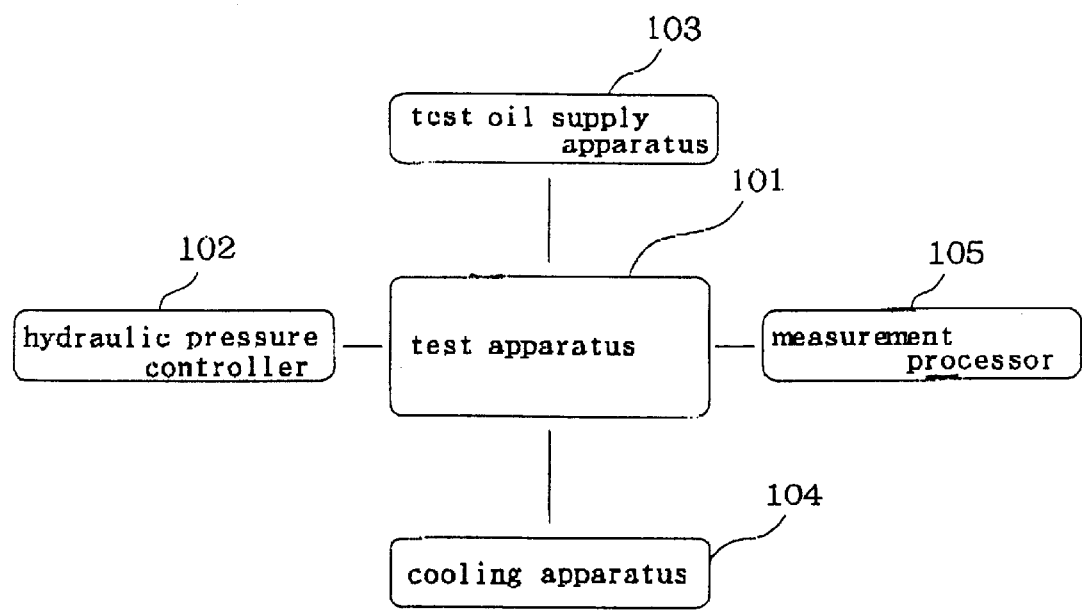
FIG. 7 is a block diagram to show a whole system.

As shown in FIG. 7, the traction coefficient measurement device comprises a test apparatus 101 in which the traction transmission is carried out under predetermined conditions, a hydraulic pressure controller 102 by which hydraulic pressure is controlled to apply a predetermined surface pressure to a traction transmission portion, a test oil supply apparatus 103 to supply to the traction transmission portion a test oil such as traction oil under temperature control, a cooling apparatus 104 to cool the load apparatus which applies a resistance to the traction section, and a measurement processor 105 to measure data in various conditions in the test apparatus 101 and process measurement data.

Figure 8:
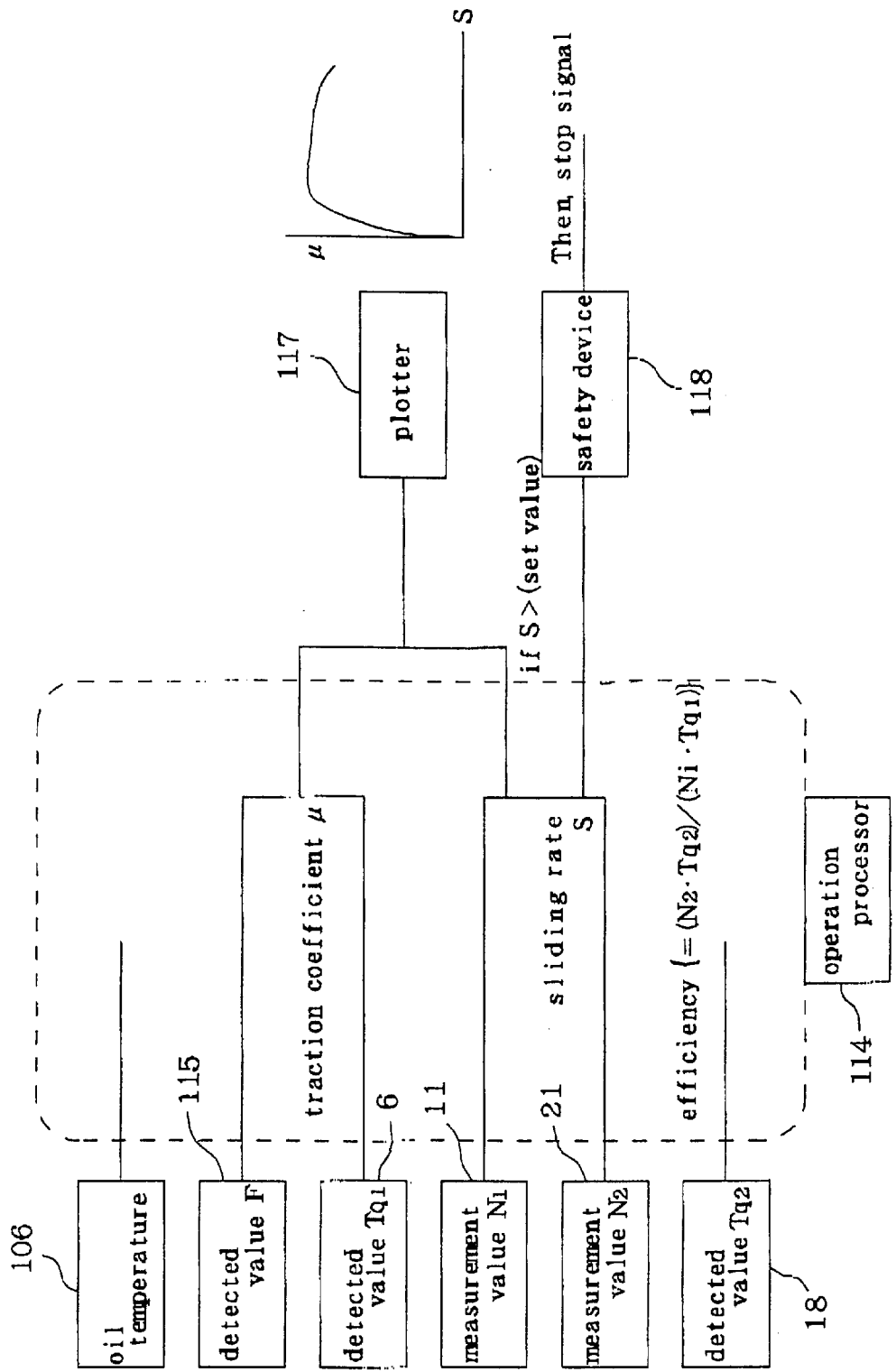
FIG. 8 is a block diagram of a measurement processing device.

The measurement processor 105 comprises, as shown in FIG. 8, an oil temperature sensor 106 to measure the temperature of the test oil to be supplied by the test oil supply apparatus 103, a load measurement device 115 to measure the load for pushing the driving roller 10 toward the driven roller 27, a torque measurement device 6 on the driving side to measure the torque transmitted through the drive shaft 5, a rotation detector 11 on the driving side to detect the rotation speed of the driving roller 10 driven by the drive shaft 5 to rotate, a rotation detector 21 on the driven side to detect the rotation speed of the driven roller 27 rotating as the driving roller 10 rotates, and a torque measurement device 18 on the driven side to measure the torque transmitted through the driven shaft 17 rotating together with the driven roller 27.

The measurement data obtained by the detection devices are, as shown in FIG. 8, input into the operation processor 114 such as microcomputer, wherein the traction coefficient $\mu$ is calculated based on the detected value F in the load measurement device 115 and the detected value $Tq_1$ in the torque measurement device 6 on the driving side.

In addition, with the operation processor 114, the slippage rate S at the traction section, that is the engagement portion between the outer peripheral surface of the driving roller 10 and the outer peripheral surface of the driven roller 27 is calculated based on the values $N_1$, $N_2$ measured at the rotation detectors 11, 21 on the driving and driven sides.

In addition, with the operation processor 114, the efficiency of power transmission $\{=(N_2 \cdot Tq_2)/(N_1 \cdot Tq_1)\}$ at the engagement portion between the outer peripheral surface of the driving roller 10 and the outer peripheral surface of the driven roller 27 is calculated based on the values Tq1, $Tq_2$ measured at the torque measurement devices 6, 21 on the driving and driven sides and the values $N_1$, $N_2$ at the rotation detectors 11, 21 on the driving and driven sides.

Figure 9:
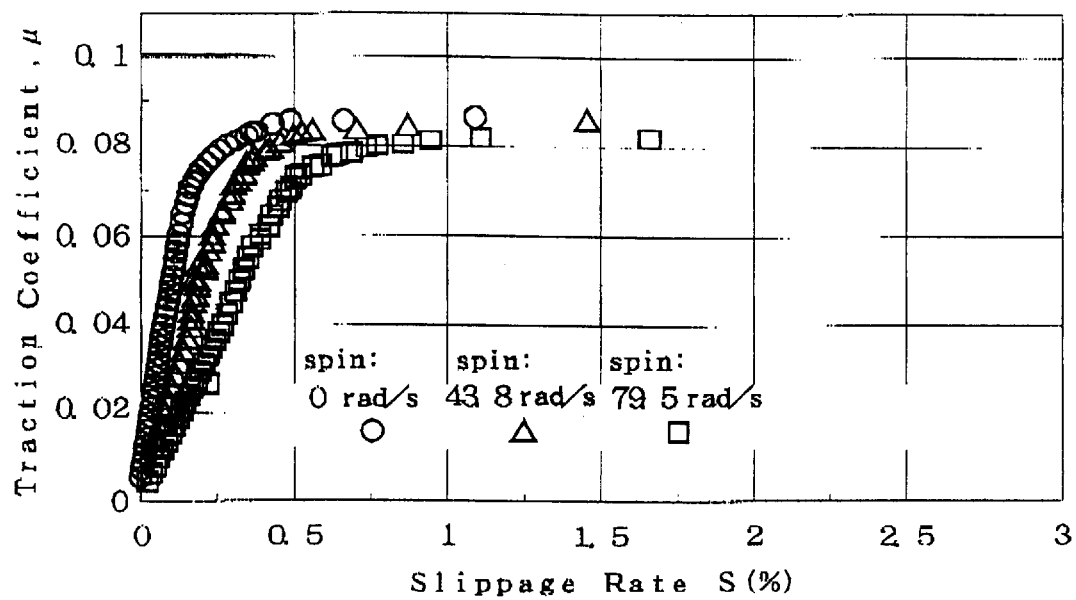
FIG. 9 is a graph to show an example of the measurement results.

In addition, with the operation processor 114, the calculated values of the traction coefficient $\mu$ and the slippage rate S are sent to the plotter 117, from which a measurement value as shown in FIG. 9 is output.

In addition, with the calculation processor 114, the sliding rate S is compared with the set value, and when the slippage rate S is higher than the set value, the test apparatus 101 is stopped by the safety device 118.

The support plate 2 for the unit on the driving side and the support plate 3 for the unit on the driven side are provided on the surface plate 1 which is the upper surface of the frame 119 in the test apparatus 101. The support plate 2 for the unit on the driving side is supported by the translation bearings 4 to be movable in the direction (up and down directions) orthogonal to the arrangement direction of the drive shaft 5. On the other hand, the support plate 3 for the unit on the driven side is supported by the pivot shaft 144 (FIGS. 4 and 5) such that its mount angle can be adjusted with respect to the surface plate 1.

The center axis O for the angle adjustment is the vertical line extending through the center of curvature of one of generatrices on the outer peripheral surface of the driven roller 27. This vertical line coincides with the tangent line vertically drawn on the circle which connects the centers of curvature to each other, at a portion close to the driving roller 10.

The drive shaft 5 is rotatably supported on the upper surface of the support pate 2 for the unit on the driving side, and has the base end 5a and the tip end 5b concentric with each other, such that the torque measurement device 6 on the driving side is provided between the both ends 5a, 5b with the couplings 7a, 7b, such that they are arranged in series.

The base end 5a is rotatably supported with a pair of rolling bearing units 8 on the upper surface of the support plate 2 for the unit on the driving side. On the other hand, the tip end 5b is rotatably supported through rolling bearings on the support bracket 9 for the driving roller which is fixed on the upper surface of the support plate 2 for the unit on the driving side and formed in a channel shape in the plan view.

The rolling bearing has a low rolling resistance, and is capable of bearing not only the radial load but also the thrust load caused by spin, and therefore comprises at least a pair of angular ball bearings in the face to face arrangement or in the back to back arrangement.

The driving roller 10 is fixed to the tip end 5b on the inside of the bracket 9 for supporting the driving roller 10. The rotation speed (rotation amount) of the tip end 5b can be detected with the rotation detector 11 on the driving side such as rotary encoder provided on the outside surface of the support bracket 9 for the driving roller.

Figure 3:
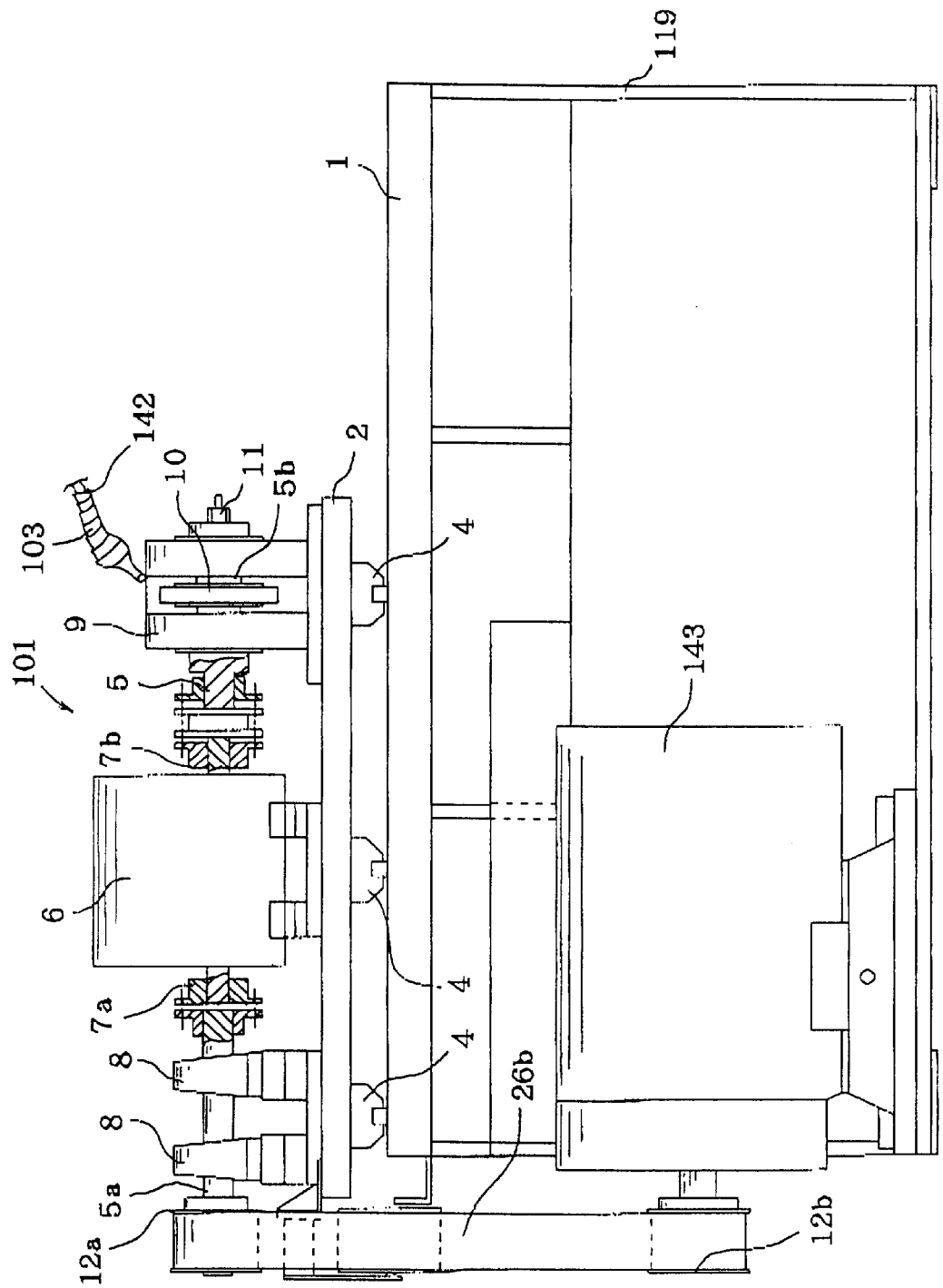
FIG. 3 is a partly cut-away, side elevational view of part of the structure of FIG. 1.

On the other hand, the driven pulley 12a is fixed to the end of the base end 5a, such that an endless belt 26b extends between the driven pulley 12a and the driving pulley 12b (FIG. 3) fixed to the rotation shaft of the motor 143 that is a driving power source, so that the driving shaft 5 is driven to rotate.

The central axis of the driving roller 10 coincides with the central axis of the drive shaft 5. The generatrices defining the outer peripheral surface of the driving roller 10 linearly extend in parallel with respect to the rotation center of the driving roller 10. Accordingly, the outer peripheral surface of the driving roller 10 defines a cylindrical surface the center of which is located in the central axis of the drive shaft 5.

The driving roller 10 is supported on the upper surface of the support plate 2 for the unit on the driving side which is in turn supported on the upper surface of the surface plate 1 through the translation bearings 4 such that it is movable in a horizontal direction and orthogonal to the direction of the arrangement of the drive shaft 5.

Provided between the upper surface of the surface plate 1 and the support bracket 9 for the driving roller 10 is a press apparatus 13 such as an air cylinder so as to press the support bracket 9 toward the driven roller 27. Specifically, the air cylinder for the press apparatus 13 has a piston rod 14 which can be moved out and in corresponding to a supply and discharge of compressed air. When the piston rod 14 is moved out, the support bracket 9 for the driving roller 10 is pressed through the load measurement device 15 such as load cell so that the contact pressure between the outer peripheral surface of the driving roller 10 and the outer peripheral surface of the driven roller 27 is increased.

On the other hand, the driven roller 27 is rotatably supported by the support bracket 16 for the driven roller which is fixed on the upper surface of the support plate 3 for the unit on the driven side, specifically in a corner thereof (left lower corner in FIG. 1).

The driven shaft 17 is rotatably supported on the upper surface of the support plate 3 for the unit on the drive side, and the base end 17c and the tip end 17b of the driven shaft 17 are concentric with each other. The torque measurement device 18 on the driven side is provided between the base end 17a and the tip end 17b with couplings 19a, 19b such that they are arranged in series. The base end 17a is rotatably supported through a pair of rolling bearing units 20 on the upper surface of the support plate 3 for the unit on the driven side, while the tip end 17b is rotatably supported through a rolling bearing in the support bracket 16 for the driven roller, which is formed in a channel shape in a plan view and fixed on the upper surface of the support plate 3 for the unit on the driven side. This rolling bearing comprises at least a pair of angular ball bearings in a back to back arrangement or in a face to face arrangement. The driven roller 27 is fixed to the tip end 17b on the inside of the support bracket 16 for the driven roller. The rotation speed (rotation amount) of the tip end 17b can be detected by way of the rotation detector 21 on the driven side such as rotary encoder which is provided on the outside surface of the support bracket 16 for the driven roller.

On the upper surface of the support plate 3 for the unit on the driven side specifically at the opposite corner thereof (right upper corner in FIG. 1), the load shaft 22 is rotatably supported with a rolling bearing unit 20a to apply a resistance against the rotation of the driven roller 27. The base end of the load shaft 22 is connected to the load apparatus 23 to provide a resistance such as electromagnetic brake against the rotation of the load shaft 22.

During the operation of the traction coefficient measurement device, the load apparatus 23 is cooled by the cooling apparatus 104. The endless belt 26a extends between the pulley 24 fixed to the tip end of the load shaft 22 and the pulley 25 fixed to an end of the base end 17a of the driven shaft 17 to apply a resistance from the load apparatus 23 to the driven roller 27.

Figure 4:
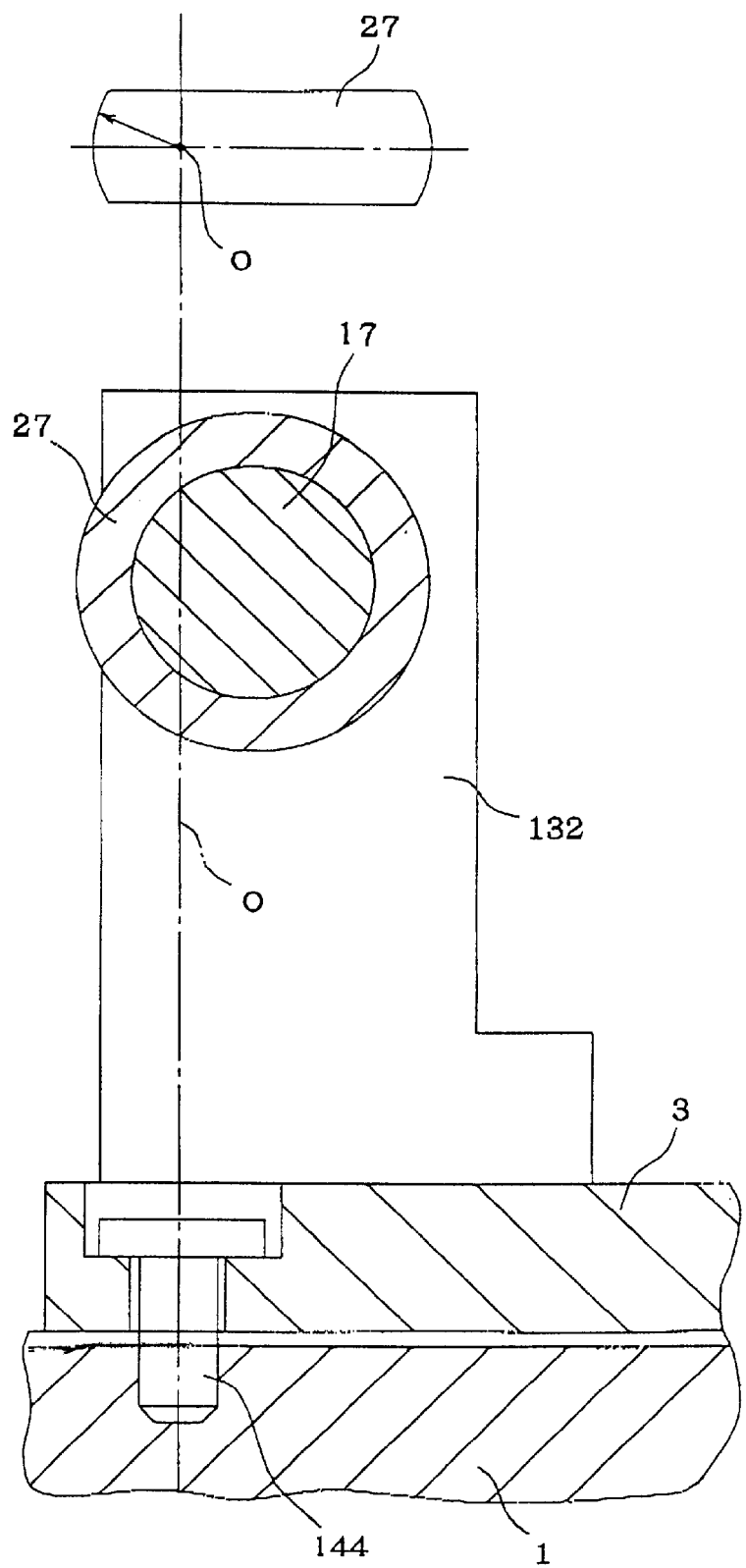
FIG. 4 is a cross sectional view taken along the line IV—IV of FIG. 1.
Figure 5A:
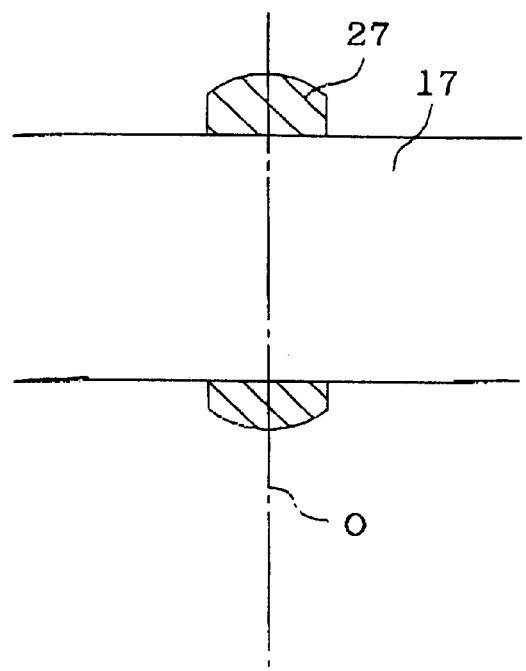
FIG. 5(A) is a left side elevational view of an upper portion of the structure of FIG. 4.
Figure 5B:
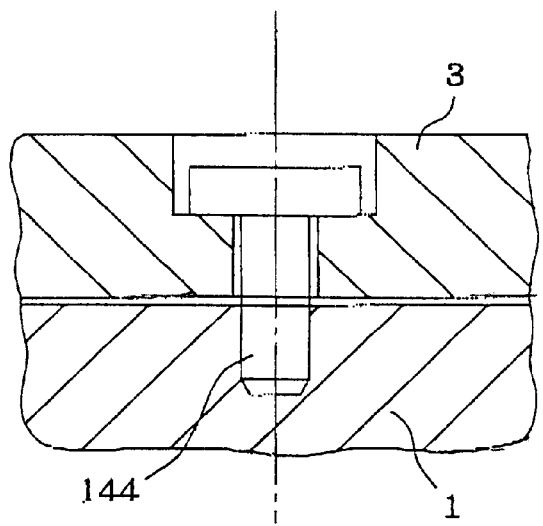
FIG. 5(B) is a left side elevational view of a lower portion of the structure of FIG. 4.
Figure 6:
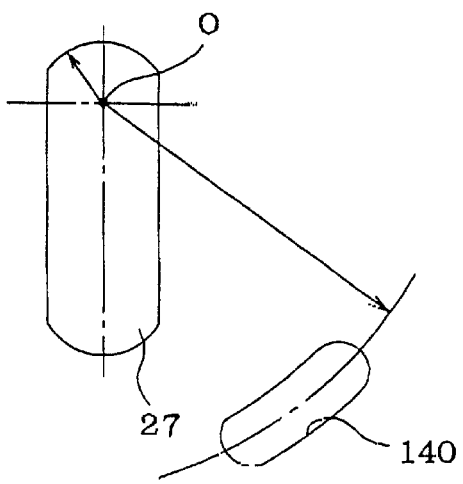
FIG. 6 is a diagram to show a relation between the driven roller and the long hole.

In this example, the generatrices defining the outer peripheral surface of the driven roller 27 are formed in an arc, respectively, to form the outer peripheral surface in a convex surface. As mentioned above, the support plate 3 for the unit on the driven side supporting the driven roller 27 is, as shown in FIGS. 4 to 6, adjustable in mount angle position with respect to the surface plate 1 through the pivot shaft 144 around the center axis O which is the vertical line extending through the center of curvature of one of the generatrices of the outer peripheral surface of the driven roller 27.

The support plate 2 for the unit on the driving side can be slidable only in a direction parallel with respect to the surface plate 1. Accordingly, the support plate 3 for the unit on the driven side can be displaced around the central axis O with respect to the support plate 2 for the unit on the driving side.

Accordingly, in the present example, a plurality of long holes 140 in an arcuate shape are formed around the central axis O, that is also the center of the pivot axis or pin 144, in the support plate 2 for the unit on the driven side. Bolts 141 are inserted into the long holes 40, and threaded into the thread holes in the surface plate 1. When the support plate 3 for the unit on the driven side is adjusted in position, the bolts 141 are loosened, and the support plate 3 is displaced around the central axis O. And, when the support plate 3 for the unit on the driven side is fixed to carry out the measurement operation, the bolts 141 are tightened.

In addition, the oil supply nozzle 142 is provided above the driving roller 10 and the driven roller 27 to supply test oil such as traction oil under temperature control to the engagement portion between the outer peripheral surfaces of the both rollers 10, 27. Specifically, the test oil such as traction oil is sprayed to the engagement portion between the outer peripheral surfaces of the both rollers 10, 27 at a predetermined temperature in the range of −40 to +150° C. from the test oil supply apparatus 103. The temperature of the test oil such as traction oil supplied to the engagement portion is measured by an oil temperature sensor 106 provided at the tip end of the oil supply nozzle 142.

When the traction coefficient is measured by the traction coefficient measurement device of the present invention, first the mount position of the support plate 3 for the unit on the driven side with respect to the surface plate 1 is controlled to produce a predetermined spin at the engagement portion between the outer peripheral surfaces of the both rollers 10, 27. The degree of the spin is smaller as the drive shaft 5 is closer to the parallel relation with the driven shaft 17 supported on the upper. surface of the support plate 3 for the unit on the driven side, and larger as the angle between the both shafts 17, 5 is larger.

In spite that the mount position of the support plate 3 for the unit on the driven side is adjusted by displacing the bolts 141 in the long holes 140 to change the degree of spin, the contact condition between the outer peripheral surfaces of the both rollers 10, 27 is kept substantially uniform.

Once the mount position of the support plate 3 for the unit on the driven side is adjusted, the test oil is supplied to the engagement portion between the outer peripheral surfaces of the both rollers 10, 27 at a predetermined temperature from the test oil supply apparatus.

Next, the support bracket 9 for the driving roller is pressed to the driven roller 27 with the press apparatus 13. As a result, a predetermined contact surface pressure $P_{max}$ is applied to the engagement portion between the outer peripheral surface of the roller 10 and the outer peripheral surface of the roller 27. The contact surface pressure $P_{max}$ is adjusted in the range of 0 to 4 Gpa, and can be adjusted with the press force by way of the press apparatus 13 and with the contact surface area between the peripheral surfaces of the both rollers 10, 27. The press force in the case of an air cylinder for the press apparatus 13 can be adjusted by changing the pressure of the compressed air supplied into the cylinder with the hydraulic pressure control device. The contact surface area can be adjusted by changing the press force, the radius of curvature of the generatrix of the outer peripheral surfaces, and the outer diameter of the both rollers 10, 27.

Next, the driving roller 10 is rotated by the motor 143 through the driving pulley 12b, the endless belt 26b, the driven pulley 12a and the drive shaft 5. The rotation speed of the driving roller 10 is adjustable in the peripheral speed range of 0 to 40 m/s by changing the rotation speed of the motor 143. When the measurement operation is carried out, a predetermined rotation speed is kept after it is accelerated to that speed. While the driving roller 10 is driven to rotate, the torque applied to the driving roller 10 is measured with the torque measurement device 6 on the driving side provided between the base end 5a and the tip end 5b of the drive shaft 5.

After the preparation as mentioned above is finished, the load apparatus 23 which has been producing no load, is operated to gradually apply load to the driven roller 27 against its rotation. The values measured at the load measurement device 15, the torque measurement device 8 on the driving side and the rotation detector 11 on the driving side are processed in the operation processor 114, and then a curve representing the relation between the slide rate S and the traction efficient $\mu$ is obtained for every spin as shown in FIG. 9 with the plotter 117.

The measurement operation for obtaining such curves is continued in real time to the so called gross slip condition where the load from the load apparatus 23 is larger, so that the driven roller 27 is not rotated while only the driving roller 10 is rotated.

Once the gross slip condition is reached, the motor 143 is stopped by the safety device 118 to avoid a situation where the operation of the test apparatus 101 is continued under the gross slip condition, and therefore damage caused to the parts of the test apparatus 101 is prevented.

The value of spin is adjustable by displacing the driven shaft 17, fixed to the driven roller 27, around the central axis O. Accordingly, the traction coefficient can be measured precisely under conditions corresponding to the practical conditions.

The torque detected with the torque measurement device 6 on the driving side contains not only the traction force caused at the contact portion between the outer peripheral surfaces of the driving roller 10 and driven roller 27, but also the dynamic torque in the rolling bearing for supporting the drive shaft 5 on the support bracket 9 for the driving roller and the dynamic torque in the rolling bearing for supporting the driven shaft 17 on the support bracket 16 for the driven roller.

In order to obtain precise traction force by eliminating the dynamic torque of the rolling bearings, it is necessary that every time before measuring the traction coefficient under a predetermined condition, the dynamic torque of the rolling bearings is measured under the same test condition. The examination of the dynamic torque of the rolling bearing provided in the torque measurement device 6 on the driving side is separately carried out according to the method predetermined for the torque measurement device 6.

The measurement of the dynamic torque of the rolling bearings is conducted after the surface pressure (pressure by the press apparatus 13) at the contact portions between the outer peripheral surfaces of the both rollers 19, 27, the peripheral speed of the outer peripheral surface of the driving roller 10, the test oil used and its temperature, the spin of the contact portion are set under a predetermined test condition with no load applied to the driven roller 27.

Under this condition, the slide rate S between the outer peripheral surfaces of the both rollers 10, 27 is 0.01% or less. Accordingly, the value of torque obtained at the torque measurement device 6 on the driving side under the operation condition is determined as the dynamic torque of the rolling bearings.

This operation is conducted specifically as follows:

First, the coupling 19b is removed from between the tip end 17b of the driven shaft 17 and the torque measurement device 18 on the driven side, so that the torque measurement device 18 and the rolling bearing units 20 are not a resistance against the rotation of the driven roller 27. In addition, the mount angle position of the support plate 3 for the unit on the driven side is adjusted, so that the value of spin at the contact portion becomes a predetermined value. Test oil controlled at a predetermined temperature is supplied to the contact portion from the oil supply nozzle 142. Next, the support bracket 9 for the driving roller is pressed to the driven roller 27 with the press apparatus 13, so that the surface pressure of the contact portion becomes a predetermined value. Then, the driving roller 10 is driven by the motor 143 and accelerated to a predetermined rotation number and then kept at the rotation number. In this condition, the operation is continued until the torque to be measured with the torque measurement device 6 on the driving side becomes stable, and the value measured at the torque measurement device 6 is recorded as the dynamic torque of the rolling bearing.

The dynamic torque of the rolling bearings obtained as mentioned above is deducted from the torque obtained in the operation of measurement of the traction coefficient, and the resulting value of torque is used to calculate the traction force produced at the contact portion between the outer peripheral surface of the driving roller 10 and the outer peripheral surface of the driven roller 27.

FIGS. 10 to 16 show another example of the embodiment of the present invention.

In this example, the outer peripheral surface of the driven roller 27 is part of the spherical surface having the center of the radius of curvature at the center of the driven roller 27. In other words, the outer peripheral surface of the driven roller 27 exists on the same spherical surface the center of curvature of which is located at the center of the driven roller 27. The pivot shaft 144 is provided for supporting the support plate 22 for the unit on the driven side with respect to the surface plate 1, such that its mount angle position is adjustable. And, the central axis O which is the center of the pivot shaft 144 is a vertical line extending through the center of the driven roller 27.

In this example constructed as mentioned above, even if the outer diameter of the driven roller 27 is changed, the support plate 3 for the unit on the driven side can be displaced around the same pivot shaft 144 with respect to the surface plate 1 when changing the spin at the contact portion between the outer peripheral surface of the driven roller 27 and the outer peripheral surface of the driving roller 10.

Figure 10:
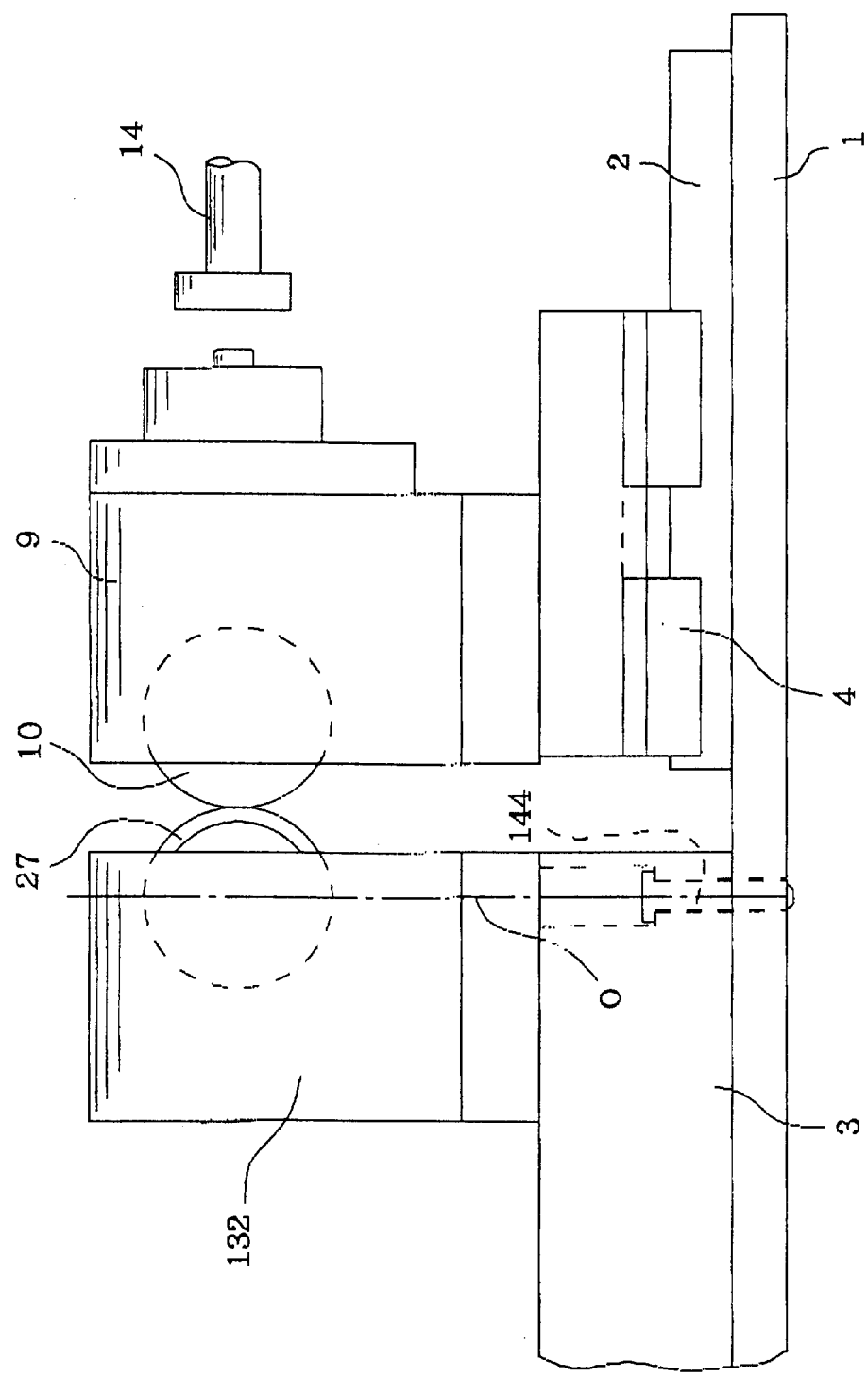
FIG. 10 is a side elevational view of another example of the embodiment of the present invention using a small diameter driven roller with some portions omitted, corresponding to the view as in Arrow X in FIG. 1.

FIG. 10 shows a condition where the driven roller 27 is relatively small in diameter to measure the traction efficient.

Figure 11:
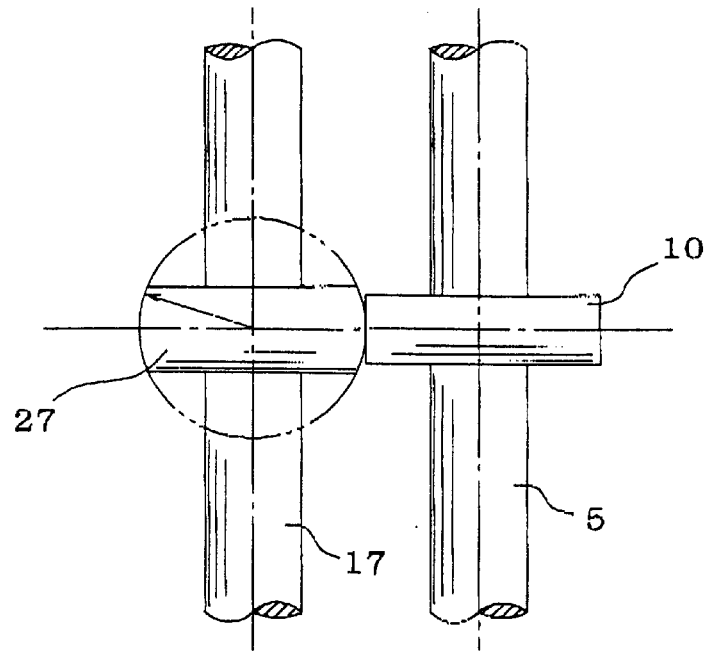
FIG. 11 is a top plan view, viewed from above in FIG. 10 with some portions omitted.
Figure 12:
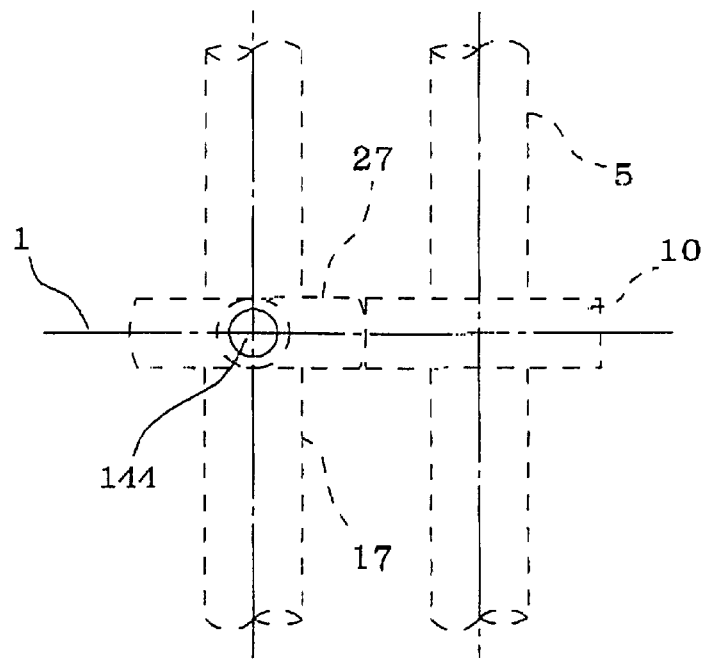
FIG. 12 is a bottom plan view, viewed from below in FIG. 10 with some portions omitted.

FIGS. 11 and 12 show a condition where the driven roller 27 is relatively small in diameter to provide the drive shaft 5 and the driven shaft 17 in a parallel relationship to make the spin zero.

Figure 13:
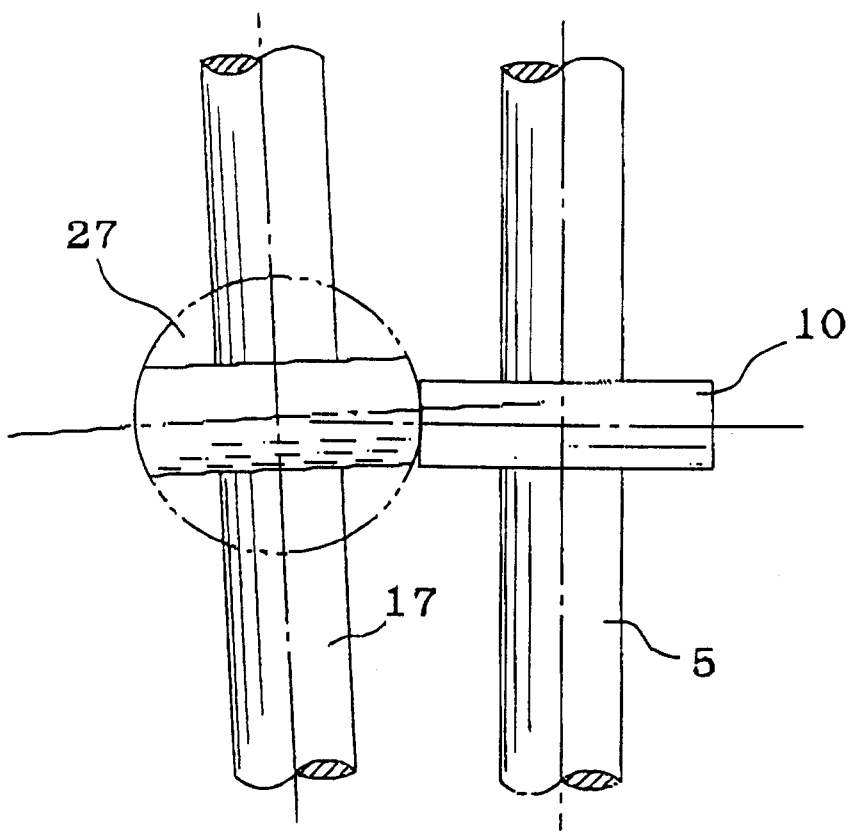
FIG. 13 is a view similar to FIG. 11, in a condition where a spin is produced.

FIGS. 13 shows a condition where the driven shaft 17 is tilted with respect to the drive shaft 5 to make the spin larger.

Figure 14:
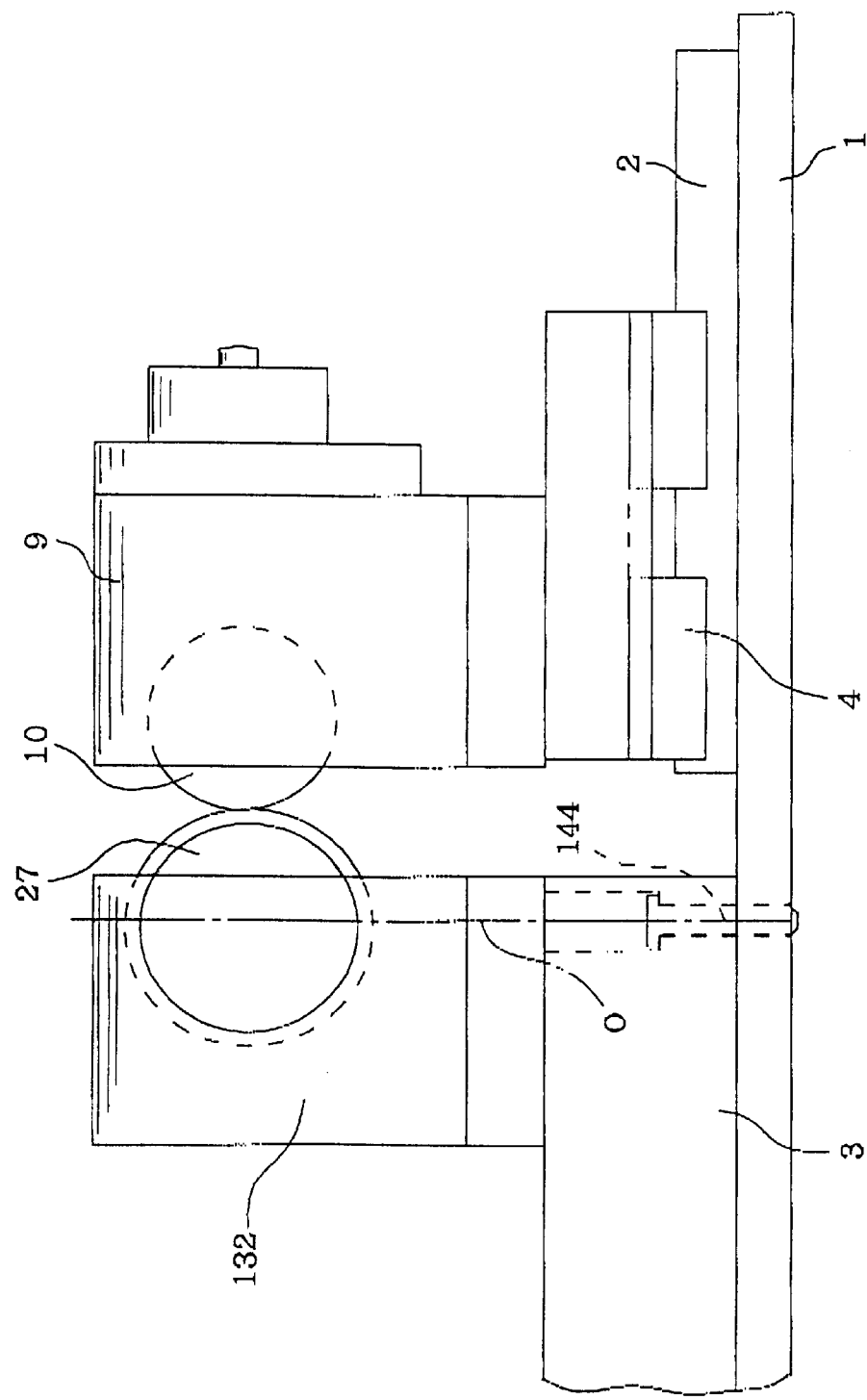
FIG. 14 is a view similar to FIG. 10, in a condition where a larger diameter driven roller is used with some portions omitted.

FIG. 14 shows a condition where the driven roller 27 is relatively large in diameter for measurement of the traction coefficient.

Figure 15:
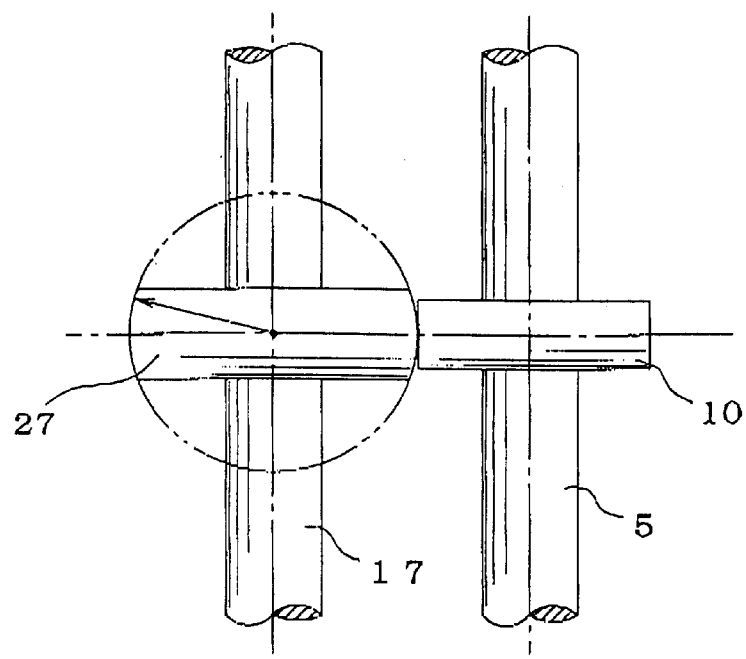
FIG. 15 is a top plan view, viewed from above in FIG. 14 with some portions omitted.

FIG. 15 shows a condition where the driven roller 27 is relatively large in diameter to provide the drive shaft 5 and the driven shaft 17 in a parallel relationship to make the spin zero.

Figure 16:
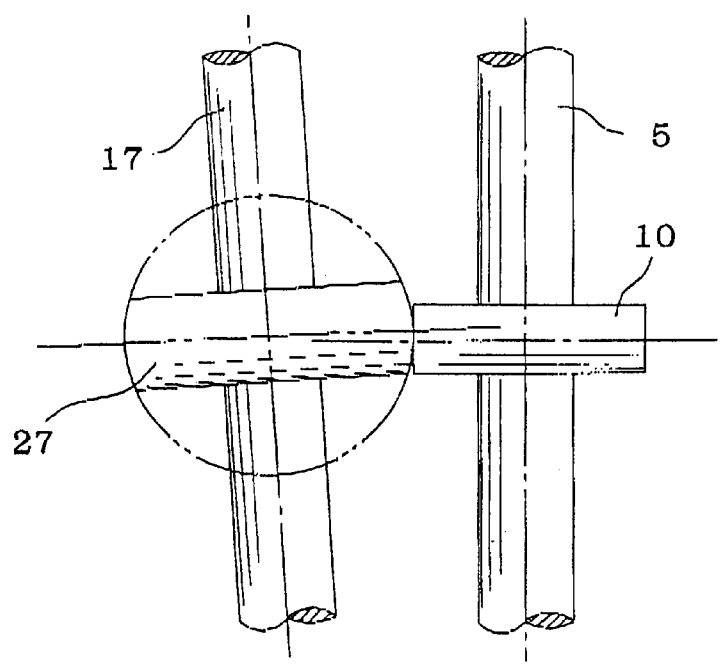
FIG. 16 is a view similar to FIG. 15, in a condition where a spin is produced.

FIGS. 16 shows a condition where the driven shaft 17 is tilted with respect to the drive shaft 5 to make the spin larger.

As clear in comparison between the examples of FIGS. 10 and 14, even if the diameter of the driven roller 27 is changed, only with the fact that the support plate 2 for the unit on the driving side is moved in parallel with the translation bearing 4, the difference in diameter between the driven rollers 27 can be absorbed.

As clear in comparison between the example of FIGS. 11 to 13 and the example of FIGS. 15 to 16, regardless of the difference in diameter between the driven rollers 27, the spin can be changed by displacing the support plate 3 for the unit on the driven side around the same pivot shaft 144.

Incidentally, in the illustrated example, the outer diameter of the driving roller 10 is not changed while the outer diameter of the driven roller 27 is changed, but the former can be changed.

In the illustrated examples, the generatrices of the outer peripheral surface of the driving roller 10 are linear, and the generatrices of the outer peripheral surface of the driven rollers 27 are arcuate in shape, which however can be contrary.

In addition, the generatrix of the outer peripheral surface of the driving roller 10, and the outer peripheral surface of the driven rollers 27 can be all arcuate in shape.

In addition, the support plate 2 for the unit on the driving side, instead of the support plate 3 for the unit on the driven side, can be displaced around the vertical pivot shaft 144 to change the spin. However, in this case, the support plate 3 for the unit on the driven side is supported by the translation bearing, and the support bracket 9 for the driven roller is pressed by the press apparatus 13.

With the traction measurement device as mentioned above, the traction coefficient can be precisely and accurately measured under the conditions corresponding to the actual operation, which leads to improvement in performance of the friction transmission apparatus.

What is claimed is:

1. A traction coefficient measurement device comprising driving and driven rollers each having an outer peripheral surface defined by generatrices, a support portion for the respective rollers, a drive shaft, and a driven shaft, the generatrices in at least one of the driving and driven rollers being formed in an arc with a center of curvature to define the outer peripheral surface of the at least one in a convex shape, the support portion for the at least one being adapted to be relatively displaced around a vertical line extending through the center of curvature of one of the generatrices one of the drive shaft and the driven shaft being fixed in position, the other being supported so as to move to and from the one shaft, and a press apparatus being used to force the other shaft to the one shaft for measurement operation, and the other shaft being positioned lower than the one shaft in vertical level, wherein the driving roller has a diameter $D_{10}$ while the driven roller has a diameter $D_{27}$, and the other shaft is positioned lower than the one shaft in vertical level by a height difference which is up to 1/2,000 of the smaller one of the diameter $D_{10}$ and diameter $D_{27}$.

2. A traction coefficient measurement device of claim 1, further comprising a pivot pin, the center of which is the vertical line extending through the curvature center of one of the generatrices.

3. A traction coefficient measuring device of claim 1, further comprising a load apparatus to apply a load to the driven roller.

4. A traction coefficient measuring device of claim 3, wherein a torque measurement device is provided between a drive source and the driving roller, and between the load apparatus and the driven roller.

5. A traction coefficient measurement device of claim 1, wherein the generatrices of the outer peripheral surface of the other of the driving and driven rollers is formed in a linear line in parallel with respect to the center of rotation of the other roller.

6. A traction coefficient measurement device of claim 1, wherein the outer peripheral surface of one of the driving and driven rollers is a portion of the spherical surface which has a radius of curvature, the center of which is located on the center of the one roller.

7. A traction coefficient measurement device of claim 1, wherein an oil supply apparatus is provided to spray traction oil at a controlled temperature on a contact portion between the outer peripheral surface of the driving roller and the outer peripheral surface of the driven roller.

8. A traction coefficient measurement device comprising:
 a drive shaft;
 a driven shaft;
 a driving roller having an outer peripheral surface and rotated together with the driving shaft by a drive source,
 a driven roller having an outer peripheral surface, such that as the outer peripheral surface of the driven roller comes into contact with the outer peripheral surface of the driving roller, the driven roller is rotated together with the driven shaft due to rotation of the driving roller,
 a load apparatus for applying to the driven shaft a resistance against the rotation of the driven shaft,
 a driving unit support plate for supporting the driving roller, and
  a driven unit support plate for supporting the driven roller,
 a surface plate on which the driving unit support plate and driven unit support plate are placed,
 a translation bearing for supporting the driving unit support plate such that the driving unit support plate can be displaced orthogonal to the direction in which the drive shaft is provided,
 a pivot shaft by which the driven unit support plate is mounted to the surface plate at a variable mount angle,
 the outer peripheral surface of the driven roller having being defined by generatrices in an arc to form the outer peripheral surface in a convex shape, and
 the driven unit support plate having the pivot shaft provided around a vertical line extending through the center of curvature of the generatrices of the outer peripheral surface of the driven roller and being possible to move around the axis of the pivot shaft.

9. The traction coefficient measurement device of claim 8, wherein the generatrices of the outer peripheral surface of the driven roller are formed in the arc to form the outer peripheral surface in the convex shape, while the generatrices of the outer peripheral surface of the driving roller are formed in a linear line in parallel to the center of rotation of the driving roller.

10. The traction coefficient measurement device of claim 8, wherein the outer peripheral surface of one of the driving roller and driven roller is formed in a partial, spherical surface the curvature center of which is located in the center of the one of the driving roller and driven roller, and wherein the vertical line extending through the center of curvature of the outer peripheral surface of the one of the driving roller and driven roller passes through the center of the one of the driving and driven roller.

11. The traction coefficient measurement device of claim 8, wherein a torque detection device is provided between the drive source and the driving roller, and between the load apparatus and the driven roller.

12. The traction coefficient measurement device of claim 8, wherein an oil supply apparatus is provided to spray traction oil under temperature control to the contact portion between the outer peripheral surface of the driving roller and the outer peripheral surface of the driven roller.

* * * * *